(12) United States Patent
Williams et al.

(10) Patent No.: US 6,497,869 B2
(45) Date of Patent: Dec. 24, 2002

(54) STABILIZED GRANULOCYTE COLONY STIMULATING FACTOR

(75) Inventors: Kathleen Brimelow Williams, Gales Ferry, CT (US); Josephine Nanette Hay, East Lyme, CT (US)

(73) Assignee: Pfizer Inc., New York, NY (US)

( * ) Notice: Subject to any disclaimer, the term of this patent is extended or adjusted under 35 U.S.C. 154(b) by 16 days.

(21) Appl. No.: 09/790,307

(22) Filed: Feb. 22, 2001

(65) Prior Publication Data

US 2002/0002133 A1 Jan. 3, 2002

Related U.S. Application Data

(60) Provisional application No. 60/185,769, filed on Feb. 29, 2000.

(51) Int. Cl.⁷ .................. A61K 38/00; A61K 45/00; A01N 37/18
(52) U.S. Cl. ............... 424/85.1; 514/12; 514/2
(58) Field of Search .............. 424/85.1; 530/351; 514/2, 12

(56) References Cited

U.S. PATENT DOCUMENTS

| | | | |
|---|---|---|---|
| 4,810,643 A | 3/1989 | Souza | 435/68 |
| 5,104,651 A | 4/1992 | Boone et al. | 424/85 |
| 5,320,840 A | 6/1994 | Camble et al. | 424/85.1 |
| 5,416,195 A | 5/1995 | Camble et al. | 530/351 |
| 5,503,827 A | 4/1996 | Woog et al. | 424/85.1 |
| 5,554,150 A | 9/1996 | Bousseau et al. | 604/89.1 |
| 5,606,024 A | 2/1997 | Boone et al. | 530/351 |
| 5,665,863 A | 9/1997 | Yeh | 530/351 |
| 5,773,581 A | 6/1998 | Camble et al. | 530/351 |
| 5,824,784 A | 10/1998 | Kinstler et al. | 530/399 |
| 5,849,883 A | 12/1998 | Boone et al. | 530/412 |
| 5,874,075 A | 2/1999 | Collins et al. | 424/85.1 |
| 5,919,443 A | 7/1999 | Michaelis et al. | 424/85.1 |
| 5,919,757 A | 7/1999 | Michaelis et al. | 514/8 |

FOREIGN PATENT DOCUMENTS

| | | | |
|---|---|---|---|
| CA | 2280449 | 2/2000 | |
| GB | 2193631 | 2/1988 | |
| GB | 2193621 | 2/1989 | A61G/9/12 |
| WO | WO9503034 | 2/1995 | A61K/9/00 |

OTHER PUBLICATIONS

Oh–eda et al, The Journal of Biological Chemistry, vol. 265, No. 20, Issue of Jul. 15, pp. 11432–11435, 1990 by the American Society for Biochemistry and Molecular Biology, Inc.—*O–Linked Sugar Chain of Human Granulocyte Colony–stimulating Factor Protects It against Polymerization and Denaturation Allowing It to Retain Its Biological Activity.*

*Primary Examiner*—Yvonne Eyler
*Assistant Examiner*—Ruixiang Li
(74) *Attorney, Agent, or Firm*—Peter C. Richardson; Gregg C. Benson; Christine S. Lee

(57) ABSTRACT

The invention relates to stable aqueous compositions of granulocyte colony stimulating factor that have a pH in the range of pH 5 to pH 8 and comprise a salt comprising sulfate ions, and to uses thereof.

20 Claims, No Drawings

STABILIZED GRANULOCYTE COLONY STIMULATING FACTOR

This application claims the benefit of priority of U.S. Provisional Application Ser. No. 60/185,769, filed Feb. 29, 2000.

FIELD OF THE INVENTION

The present invention is directed toward aqueous compositions of granulocyte colony stimulating factor (G-CSF), particularly non-glycosylated G-CSF, having a pH of from about 5.0 to about 8.0, and a salt comprising sulfate ions at a concentration of from about 0.01M to about 1.0M.

The presence of the salt comprising sulfate ions unexpectedly stabilizes non-glycosylated G-CSF in an aqueous composition having a pH from about 5.0 to about 8.0.

BACKGROUND OF THE INVENTION

Colony stimulating factors induce proliferation, development and maturation of specific haematopoietic cells. G-CSF, in particular, leads to enhanced levels of circulating polymorphonuclear neutrophils (PMN), which play critical roles in the destruction of infectious agents. Human granulocyte colony stimulating factor (hG-CSF), for example, is used to stimulate haematopoiesis to protect patients undergoing bone marrow-suppressive chemotherapy against opportunistic infections.

G-CSF may also be used to afford similar protection for domesticated animals such as cattle, dogs, and cats. Infectious diseases in cattle and milk-producing cows, including shipping fever and bovine mastitis respectively, are a source of significant, persistent economic losses.

Shipping fever encompasses a collection of respiratory ailments afflicting cattle that are often detected in stressed animals within a population assembled from a number of different sources into a feed lot. The initial infections, generally caused by mycoplasma, chlamydia, bacteria, viruses, or mixtures thereof, are highly contagious and, although usually not lethal, they leave the animal in a debilitated state. Subsequent infection by another, opportunistic organism, especially *Pasteurella haemolytica*, is often the cause of mortality under these circumstances, rather than the initial infection. Bovine mastitis refers to an infection of the udders that may be caused by either gram negative or gram positive organisms. These infections are also highly contagious and may lead to a significant reduction in milk production by the affected cow, and, if scarring occurs, this loss may be permanent. Accordingly, methods and compositions that permit successful treatment of domesticated species with G-CSF could prevent or ameliorate the effects of such infectious diseases in such commercially important animals.

Mature bovine granulocyte colony stimulating factor, bG-CSF (GenBank Accession Number AF0925333), consists of 174 amino acids, of which 82% are identical with those in the corresponding human protein (GenBank Accession Number M17706). Both the human and bovine granulocyte colony stimulating factors are hydrophobic proteins, which include an odd number (five) of cysteine residues. Consequently, at least one of the cysteine side chains will present a free thiol moiety that may lead to the formation of untoward intramolecular and intermolecular disulfide linkages, resulting in the accumulation of insoluble, biologically inactive, dimeric or polymeric structures. This hypothesis has been proposed as one possible explanation for the observation that hG-CSF, bG-CSF and other G-CSF molecules, particularly recombinant, non-glycosylated forms produced in prokaryotic hosts, are difficult to formulate as stable, pharmaceutically acceptable compositions.

Glycosylated hG-CSF has been compared with de-glycosylated hG-CSF, prepared by in vitro enzymatic digestion with neuraminidase and endo-$\alpha$-N-acetylgalactosaminidase, with respect to its stability as a function of pH and temperature (Oh-eda et al., 1990, *J. Biol. Chem.* 265 (20): 11432–35). The de-glycosylated hG-CSF, dissolved at a concentration of 1 $\mu$g/mL in 20 mM phosphate buffer containing 0.2 M NaCl and 0.01% Tween 20 was rapidly inactivated within the pH range of from about pH 7 to about pH 8 after a two-day incubation at 37° C. In contrast, glycosylated hG-CSF retained over 80% of its activity under the same conditions. Furthermore, evaluation of the thermal stability of both forms of hG-CSF, measured by biological assay and calorimetric analysis, indicated that de-glycosylated hG-CS F was less thermally stable than the native form of hG-CSF.

A number of approaches have been taken in order to provide stable, pharmaceutically acceptable G-CSF compositions. One approach to improving the composition stability of G-CSF involves the synthesis of derivatives of the protein. U.S. Pat. No. 5,665,863 to Yeh (the "'863 patent") discloses the formation of recombinant chimeric proteins comprising G-CSF coupled with albumin, which have new pharmacokinetic properties. U.S. Pat. No. 5,824,784 to Kinstler et al. (the "'784 patent") and U.S. Pat. No. 5,320,840 to Camble et al., (the "'840 patent") disclose the chemical attachment of water-soluble polymers to proteins to improve stability and provide protection against proteolytic degradation. More specifically, the '784 patent discloses N-terminally modified G-CSF molecules carrying chemically attached polymers, including polyethylene glycol.

An alternative approach to increasing stability of G-CSF in composition involves alteration of the amino acid sequence of the protein. U.S. Pat. No. 5,416,195 to Camble et al. (the "'195 patent") discloses genetically engineered analogues of G-CSF having improved composition stability, wherein the cysteine residue normally found at position 17 of the mature polypeptide chain, the aspartic acid residue found at position 27, and at least one of the tandem proline residues found at positions 65 and 66, are all replaced with a serine residue. Furthermore, U.S. Pat. No. 5,773,581 to Camble et al. (the "'581 patent") discloses the genetically engineered G-CSF analogues of the '195 patent that have been covalently conjugated to a water soluble polymer.

Other approaches to improving the composition stability of G-CSF molecules have involved modification of the solvent in which the G-CSF is dissolved. U.S. Pat. No. 5,104,651 to Boone et al. (the "'651 patent") discloses improved stability of G-CSF under conditions of low pH and minimal ionic strength. The '651 patent discloses a stabilized pharmaceutically acceptable composition consisting essentially of a pharmaceutically acceptable amount of G-CSF and acid, where the composition has a pH of 3.0 to 3.7 and a conductivity of less than 1000 $\mu$mhos/cm. In a preferred embodiment of this invention, no salt, other than a residual trace derived from the purification process, will be included in the composition.

U.S. Pat. No. 5,874,075 to Collins et al. (the "'075 patent") discloses stable compositions of proteins, including G-CSF, comprising a liposome vesicle composed of negatively charged phospholipids, where only a portion of the protein is inserted into the lipid portion of the vesicle. The '075 patent also discloses compositions comprising liposome vesicles combined with G-CSF that has been covalently linked with polyethylene glycol.

A stable G-CSF containing composition is disclosed in GB 2193621 A (the "'621 application), which comprises at least one substance selected from the group consisting of a pharmaceutically acceptable surfactant, saccharide, protein and a high-molecular weight compound. Suitable high-molecular weight compounds include hydroxypropyl cellulose, hydroxymethyl cellulose, sodium carboxymethyl cellulose, polyethylene glycol, polyvinyl alcohol, and polyvinylpyrrolidone. Proteins deemed useful in the compositions of the '621 application include human serum albumin, human serum globulin, gelatin, acid-treated gelatin, and alkali-treated gelatin.

U.S. Pat. No. 5,503,827 to Woog et al. (the "'827 patent") discloses pharmaceutical preparations of G-CSF that include at least one bactericidal preservative selected from the group consisting of chlorobutanol, benzyl alcohol, benzalkonium chloride and mixtures thereof. Pharmaceutical preparations of the '827 patent may also include auxiliary substances, examples of which are stabilizing agents and organic hydrophilic polymers. Useful stabilizers disclosed by the '827 patent encompass oligosaccharides such as sucrose, lactose and dextrans with a molecular weight of about 10,000 to 2,000,000. Useful organic hydrophilic polymers include polyethylene glycol and polyvinylpyrrolidone.

U.S. Pat. No. 5,919,757 to Michaelis et al. (the "'757 patent") discloses aqueous pharmaceutical preparations of G-CSF that are stable on storage, which comprise a buffer selected from the group consisting of citrate, maleate, a mixture of citrate and phosphate, arginine and arginine salts, and at least one surfactant, where the pH of the composition is from about pH 7 to pH 8. The '757 patent discloses that particular pH ranges of the liquid pharmaceutical preparation, in a mixture with a particular buffer result in particularly stable compositions. Furthermore, the '757 patent discloses that it is not advantageous to add salts, since high concentrations of salts or ions promote the formation of G-CSF aggregates. The '757 patent also discloses that, accordingly, buffer concentrations are calculated so that the pH-stabilizing effect is achieved but the ionic strength is kept as small as possible, with buffer concentrations preferably in the range of up to 80 mM, and particularly preferably of less than 30 mM.

U.S. Pat. No. 5,919,443 to Michaelis et al. (the "'443 patent") discloses lyophilized and reconstituted pharmaceutical preparations comprising G-CSF, a stabilizing agent selected from the group consisting of maltose, cellobiose, gentibiose, isomaltose and sucrose, and a surfactant that is present in an amount no greater than the amount of G-CSF present in the composition. The preparations of the '443 patent have a pH within the range of pH 7 to pH 8, and are free of human serum albumin and polymers. The '443 patent also discloses it may be expedient to add auxiliary substances, which are mainly non-ionized, to provide an isotonic pharmaceutical preparation. The '443 patent further indicates that it is not advantageous to add salts to adjust the isotonicity, as high concentrations of salts or ions promote formation of G-CSF aggregates and, accordingly, salts are added in small amounts.

PCT International Publication No. WO 95/03034 (the "'034 publication") discloses stabilized aqueous compositions of G-CSF to be administered as aerosols, comprising a polar organic compound, which reduces the surface tension of water to no greater than about 65 dynes/centimeter, or a surfactant which reduces the surface tension of water to no greater than about 40 dynes/centimeter. The '034 publication discloses preferred polar organic solvents that include polyethylene glycol and methyl pentanediol, and a preferred surfactant, Tween 80. Compositions disclosed in the '034 publication may include a buffer or, simply, aqueous hydrochloric acid, such that the pH is adjusted to fall within the range of pH 2.5 to pH 5.5.

U.S. Pat. No. 5,554,150 to Bousseau et al. (the "'150 patent") discloses compositions suitable for subcutaneous, continuous administration of G-CSF. The G-CSF compositions of the '150 patent comprise granulocyte colony stimulating factor, serum albumin, a non-ionic surface-active agent, a saccharide, disodium phosphate, monosodium phosphate, and sodium chloride.

Solution folding of proteins is influenced by the presence of one or more salts, which may interact with both the protein and the solvent. Ionic components of salts may interact directly with the charged amino acid side chains or dipolar peptide bonds of the protein, and they may also affect the structure of the solvent, thereby influencing the interaction between the dissolved protein and the solvent. The nature of these interactions is influenced by the specific protein, its concentration, the temperature and pH of the solution, the particular salt used and the concentration of that salt. These features may be exploited for example, to allow the selective precipitation of polypeptides as part of a protein purification process. Hydrophobic proteins, which are inherently less water soluble, are particularly sensitive to aggregation and precipitation in the presence of salt, and therefore, as exemplified by the '443, '757, and '651 patents, prior art G-CSF compositions have deliberately avoided the addition of salt.

SUMMARY OF THE INVENTION

The present invention is directed toward stabilized aqueous compositions of G-CSF. The invention provides unexpectedly stable aqueous compositions comprising G-CSF, particularly non-glycosylated G-CSF, having a pH of from about 5.0 to about 8.0, and a salt comprising a sulfate ion. The aqueous composition may also comprise at least one buffering agent. The concentration of G-CSF, particularly non-glycosylated G-CSF, in any of the compositions described herein is preferably at least about 0.01 mg/mL and the concentration of the salt comprising sulfate ions in the compositions is preferably from about 0.01M to about 1.0M; preferred concentrations are at least about 0.01 mg/mL non-glycosylated G-CSF and at least 0.1M of the salt comprising sulfate ions. In an embodiment of any of the compositions described herein, the granulocyte colony stimulating factor is selected from the group consisting of bovine granulocyte colony stimulating factor, canine granulocyte colony stimulating factor, feline granulocyte colony stimulating factor, and human granulocyte colony stimulating factor.

The present invention is also directed to a method of treating disease in a mammal, comprising administering to a mammal in need of such treatment, a therapeutically effective dose of granulocyte colony stimulating factor in an aqueous composition having a pH of from about 5.0 to about 8.0, which aqueous composition comprises a salt comprising sulfate ions, wherein the salt is present at a concentration of from about 0.01M to about 1.0M. In other embodiments, the aqueous composition comprises any of the above-described compositions. In an embodiment of the method, the mammal is a canine mammal. In another embodiment of the method, the mammal is a feline mammal. In another embodiment of the method, the mammal is a human. The invention is also directed to a method of treating disease or conditions alleviated by stimulation of haematopoiesis. In an embodiment, the method is used to alleviate the effects of bone-marrow suppressive therapy, as in cancer treatments. In an embodiment of the method, the disease is granulocytopenia. In another embodiment of the method, the disease is an infectious disease. In a preferred embodiment of the method, the mammal is a bovine mammal. In a more preferred embodiment of the method, the infectious disease is shipping fever or bovine mastitis, and the mammal is a bovine mammal. The invention also relates to the use of an aqueous composition as provided herein, for the preparation of a medicament for the treatment in a mammal, preferably a bovine mammal or a human, of a disease, such as granulocytopenia or an infectious disease, as described further herein.

The present invention may be understood more fully by reference to the detailed description and illustrative examples, which are intended to exemplify non-limiting embodiments of the invention.

DETAILED DESCRIPTION OF THE INVENTION

The present invention is directed toward aqueous compositions comprising non-glycosylated G-CSF that comprise from about 0.01M to about 1.0M of a salt comprising sulfate ions, and having a pH of from about 5 to about 8. Such aqueous compositions exhibit unexpectedly improved stability.

As used herein, "G-CSF" refers to a protein that has the sequence of a naturally occurring mammalian granulocyte colony stimulating factor. The production of recombinant non-glycosylated bG-CSF is described in U.S. Pat. No. 5,849,883. The production of non-glycosylated human G-CSF ("hG-CSF") is described in U.S. Pat. No. 4,810,643 and the production of non-glycosylated canine G-CSF is described in U.S. Pat. No. 5,606,024. The G-CSF of other mammalian species can be cloned and expressed using the procedures set forth in the above noted patents concerning bovine and canine G-CSF.

As used herein, G-CSF encompasses structural analogues of this protein having one or more amino acid substitutions, additions or deletions. Also contemplated by the term G-CSF, as used herein, are portions or fragments of the mature protein which retain at least one of the biological activities of the intact molecule, whether used alone or formed as part of a chimeric protein, however constructed. Furthermore, as used herein, G-CSF also encompasses derivatives ("muteins") of G-CSF wherein at least one residue has been replaced with another amino acid. Included are derivatives in which at least one of the following amino acid substitutions has been made (amino acid numbering is in reference to the mature protein; therefore where an N-terminal methionine is present, it is assigned position −1 or 0): $Cys^{17}$ of the native sequence replaced by a $Ser^{17}$ residue, $Asp^{27}$ of the native sequence replaced by a $Ser^{27}$ residue, $Leu^{15}$ of the native sequence replaced by a $Glu^{15}$ residue, $Lys^{23}$ of the native sequence replaced by an $Arg^{23}$ residue, $Gly^{28}$ of the native sequence replaced by an $Ala^{28}$ residue, $Lys^{40}$ of the native sequence replaced by an $Arg^{40}$ residue, $Pro^{44}$ of the native sequence replaced by an $Ala^{44}$ residue, $Leu^{49}$ of the native sequence replaced by a $Lys^{49}$ residue, $Gly^{55}$ of the native sequence replaced by an $Ala^{55}$ residue, $Cys^{60}$ of the native sequence replaced by a $Ser^{60}$ residue, $Pro^{111}$ of the native sequence replaced by a $Glu^{111}$ residue, $Thr^{115}$ of the native sequence replaced by a $Ser^{115}$ residue, and $Tyr^{165}$ of the native sequence replaced by an $Arg^{165}$ residue. Such derivatives are described in U.S. Pat. No. 5,416,195, which is included herein by reference, in its entirety.

Suitable salts comprising sulfate ions, which are preferably inorganic sulfate salts, comprise sulfate ions and at least one suitable cation, which may be selected from the group consisting of alkali metal ions, alkaline earth metal ions, and ammonium ion. Preferred salts comprising sulfate ions are selected from the group consisting of ammonium sulfate, sodium sulfate, magnesium sulfate, and mixtures thereof. The most preferred salt comprising sulfate ions is ammonium sulfate. Suitable concentration ranges for the salt comprising sulfate ions in the aqueous compositions are from about 0.01 M to about 1.0M, preferably from about 0.025M to about 0.5M, more preferably from about 0.05M to about 0.25M, and most preferably greater than 0.1M but less than about 1.0M. Salts comprising sulfate ions useful in the present invention include those salts, whether anhydrous or hydrated, that are sufficiently water-soluble to provide aqueous compositions having a concentration of at least about 0.1M at 20° C. at neutral pH.

G-CSF can be dissolved in the subject aqueous compositions to provide a therapeutically effective dose when a pharmaceutically acceptable volume is administered to the animal. The concentration of non-glycosylated G-CSF, particularly non-glycosylated G-CSF, in the present aqueous compositions is suitably from about 0.01 mg/mL to about 10 mg/mL, preferably from about 0.1 mg/mL to about 7.5 mg/mL, and more preferably from about 1 mg/mL to about 5 mg/mL.

Suitable pH values for the aqueous compositions of the present invention are from about pH 5 to about pH 8, and preferably from about pH 6 to about pH 7.5. Suitable buffering agents that are advantageously used to maintain the pH of the subject aqueous compositions include acetate, citrate, and phosphate. Alternative buffering agents include buffers containing sulfonate moieties, such as HEPES, BES, TAPS, EPPS, TES, and mixtures thereof. Generally, the buffering agent chosen has a $pK_a$ within 1 pH unit, and preferably within 0.5 pH unit, of the pH value chosen for the G-CSF aqueous composition. In some instances, buffering agents may be used at a concentration of up to about 1 M, although as used herein the buffering agents are generally used in the present compositions at a concentration within the range of from about 1 mM to about 100 mM, preferably from about 5 mM to 50 mM and, most preferably at about 10 mM.

The method of preparation of the subject aqueous compositions is not critical. For example, aqueous compositions can be prepared by dissolving G-CSF, which, for example, may be provided as a lyophilized powder, in water, followed by the addition of aliquots of concentrated stock compositions or solid reagents, pH adjustment as necessary with an acid or base, and addition of water to bring the aqueous composition to an appropriate final volume. Alternatively, the G-CSF can be dissolved in a previously prepared aqueous composition, which may comprise a suitable buffering agent and a salt comprising sulfate ions. The subject aqueous compositions may also be prepared by adding aliquots of concentrated stock solutions or solid reagents to an aqueous composition of G-CSF to provide a stabilized G-CSF composition. Other methods for preparing the aqueous compositions of the present invention include dialysis or ultrafiltration of G-CSF compositions against an aqueous composition, which may comprise one or more buffering agents and one or more salts comprising sulfate ions of the present invention.

The aqueous compositions of the present invention may also comprise other pharmaceutically acceptable solutes including additives and other therapeutic agents, as appropriate. Suitable additives are those well known in the art including, but not limited to, antioxidants, antibacterials, surfactants, chelating agents, sugars, and preservatives.

The present aqueous compositions can be lyophilized and stored as powders or lyophilisates until needed and then redissolved in an aqueous medium.

The aqueous compositions of the invention can be administered by injection, which can be intramuscular, intravenous or preferably subcutaneous. A dose of from about 0.5 $\mu$g/Kg/day to about 10 $\mu$g/Kg/day, preferably from about 1 $\mu$g/Kg/day to 5 $\mu$g/Kg/day, can be used to induce granulocytosis and reverse granulocytopenia. Generally, the dose and mode of administration of the aqueous compositions of the invention are the same as conventional bG-CSF compositions.

The following examples illustrate the compositions and methods of the present invention. It is to be understood that the present invention is not limited to the specific details of the Examples provided below.

EXAMPLES

In each of the following examples, lyophilized, surfactant-free bG-CSF, was dissolved in water or an aqueous composition comprising a buffering agent and a salt, as indicated. Bovine granulocyte colony stimulating factor employed in each example was produced in a recombinant DNA process using an *E. coli* expression system, and purified using standard materials and procedures. Where used, phosphate and citrate buffers were in the sodium form.

Protein stability was evaluated after incubation of samples of the aqueous composition of bG-CSF to be tested at 40° C.

4.6×250 mm) run for 55 minutes with a mobile phase gradient of from 70% A: 30%B to 30% A: 70%B, run with a flow rate of 1 mL/min., where A=0.1% trifluoroacetic acid in water and B=0.1% trifluoroacetic acid in acetonitrile. Samples were monitored by UV absorption at 220 nm, and quantitation established relative to G-CSF standards formulated to concentrations of 0.05 to 0.15 mg/mL.

Samples were also analyzed by differential scanning calorimetry ("DSC") using a MicroCal VP-DSC Micro-Calorimeter. Samples were scanned by DSC between the starting temperature of 20° C. and 90° C. using a scan rate of 60° C./hr. The postscan thermostat was set at 25° C., which was established over a 15 min. period. Samples were filled at a temperature of 20° C. to 25° C. with the prescan thermostat set to 20° C., which was established over a 5 min. period. The filtering period was 16 sec., the feedback mode was set as "low" and single scans were run for each sample examined.

Example 1

Substantial loss of bG-CSF was observed where this protein was dissolved in unbuffered water and incubated at a temperature of 40° C. Stability was significantly increased where the aqueous composition was buffered at a low pH, for example at pH 4 using 10 mM sodium citrate as the buffering agent. In contrast, bG-CSF was distinctly unstable when formulated in an aqueous medium at a neutral pH using, for example, 10 mM sodium phosphate as the buffering agent at pH 7. Unexpectedly, it has been discovered that aqueous compositions of bG-CSF comprising a 10 mM sodium phosphate buffer at pH 7, when supplemented with 0.1 M ammonium sulfate, were remarkably stable as demonstrated in Table 1.

Table 1 presents the effect of salts on the stability of bG-CSF in the indicated aqueous compositions. Data are reported as percent of initial concentration of bG-CSF (0.5 mg/mL bG-CSF) remaining as a function of time at 40° C. The reported values are generally an average of at least two determinations.

TABLE 1

| Vehicle | Day Zero | Day Three | Day Six | Day Ten | Day Twelve | Day Seventeen |
| --- | --- | --- | --- | --- | --- | --- |
| Water pH 5 | 100 | 82 | 73 | 63 | 61 | 47 |
| 10 mM $Na_3C_6H_5O_7$ pH 4 | 100 | 89 | 83 | 79 | 86 | 73 |
| 10 mM Phosphate Buffer pH 7 | 100 | 12 | 9 | 0 | 0 | 0 |
| 10 mM Phosphate Buffer pH 7 and 100 mM $(NH_4)_2SO_4$ | 100 | 89 | 82 | 77 | — | 68 |
| 10 mM Phosphate Buffer pH 7 and 100 mM NaBr | 100 | 58 | 38 | 23 | — | 11 |
| 10 mM Phosphate Buffer pH 7 and 100 mM $NaC_2H_3O_2$ | 100 | 48 | 35 | 25 | — | 12 |
| 10 mM Phosphate Buffer pH 7 and 100 mM $Na_3C_6H_5O_7$ | 100 | 89 | 81 | — | 62 | 52 |
| 10 mM Phosphate Buffer pH 7 and 100 mM NaI | 100 | 41 | 20 | — | 0 | 0 |
| 10 mM Phosphate Buffer pH 7 and 100 mM $NaClO_4$ | 100 | 49 | 23 | — | 8 | 16 |

At the end of the indicated time period, aliquots of the samples were removed, diluted five-fold to a concentration of 0.10 mg/mL with MilliQ® water, and filtered through a 0.22 $\mu$m membrane filter, where, applicants believe, insoluble, aggregated forms of bG-CSF were removed, before injection onto Reverse Phase HPLC columns. Filtered aliquots of the samples were analyzed by reverse phase HPLC as follows: 100 $\mu$L samples were injected onto a Phenomenex Jupiter® $C_4$-reverse phase column (5 $\mu$m, The results show that the stability of bG-CSF at pH 7.0 in 0.1M $(NH_4)_2SO_4$ is unexpectedly comparable to the stability of bG-CSF in a citrate buffer at pH 4.0.

Example 2

Differential Scanning Calorimetry ("DSC") allows the detection of conformational changes (e.g. unfolding, secondary structure conversion, or intra-molecular association)

in the protein by measuring the change in heat capacity of the sample as a function of temperature. This provides information not only on the structural changes undergone under different conditions as a function of temperature, but also on the relative thermal stability of the protein as a function of formulation conditions, through comparison of the unfolding temperatures. Accordingly, protein thermal stability in a specified composition, therefore can be assessed by determining the $T_m$ of the protein under those conditions. As a protein composition is gradually heated, the heat capacity changes as the dissolved polypeptide unfolds. This change in heat capacity plotted as a function of temperature, yields a curve, and the temperature at which half-maximal increase in ultraviolet absorption is observed is designated the $T_m$. Accordingly, the value of the $T_m$ observed is a reflection of the thermal stability of the protein, as formulated in that composition. As shown in Table 2, the $T_m$ of bG-CSF was 4.8° C. higher when dissolved in a sodium citrate buffer at pH 4, than when dissolved in unbuffered water. As demonstrated below in Table 2, a comparable increase in $T_m$ was observed for an aqueous composition comprising bG-CSF, 10 mM sodium phosphate buffer at pH 7 and 0.1 M ammonium sulfate.

Table 2 presents the effect of different salts on bG-CSF thermal stability in the indicated aqueous compositions. Data are reported as the denaturation temperature of the protein dissolved in each aqueous composition (the higher the $T_m$, the greater the degree of stabilization). The aqueous compositions were formulated with 0.5 mg/mL bG-CSF.

TABLE 2

| Vehicle | $T_m$ - Trial 1 | $T_m$ - Trial 2 | Average | Standard Deviation |
|---|---|---|---|---|
| 100 mM $(NH_4)_2SO_4$ 10 mM $NaH_2PO_4$ pH 7 | 57.4° C. | — | — | — |
| 100 mM NaI 10 mM $NaH_2PO_4$ pH 7 | 52.5° C. | 52.2° C. | 52.4° C. | 0.2° C. |
| 100 mM NaBr 10 mM $NaH_2PO_4$ pH 7 | 53.2° C. | — | — | — |
| 100 mM $NaC_6H_5O_7$ 10 mM $NaH_2PO_4$ pH 7 | 53.8° C. | 53.7° C. | 53.7° C. | 0.01° C. |
| 10 mM $NaC_6H_5O_7$ Buffer, pH 4.0 | 57.2° C. | 57.1° C. | 57.1° C. | 0.1° C. |
| Water pH 5.2 | 52.4° C. | — | — | — |
| 100 mM $NaCH_3CO_2$ 10 mM $NaH_2PO_4$ pH 7 | 52.0° C. | 52.5° C. | 52.3° C. | 0.3° C. |
| 100 mM $NaClO_4$ 10 mM $NaH_2PO_4$ pH 7 | 51.6° C. | 51.7° C. | 51.7° C. | 0.1° C. |

These results confirm that the stability of G-CSF at pH 7 in 0.1M $(NH_4)_2SO_4$ is comparable to the stability of G-CSF at pH 4.0 in citrate buffer.

Example 3

The data in Table 3 demonstrate the stabilizing effect of salts comprising sulfate ions on bG-CSF compositions as a function of pH.

Table 3 presents the effects of pH on the stability of bG-CSF in the presence and absence of ammonium sulfate (100 mM) and sodium bromide (100 mM). The buffering agent used in each aqueous composition was 10 mM sodium citrate. Aliquots of each sample were analyzed by RP-HPLC, with the data reported as % initial concentration of bG-CSF as a function of time at 40° C. The aqueous compositions were formulated with 0.5 mg/mL bG-CSF.

TABLE 3

| Vehicle | Day Zero | Day Three | Day Six | Day Twelve | Day Seventeen | Day Thirty-three |
|---|---|---|---|---|---|---|
| 10 mM $Na_3C_5H_6O_7$ - pH 4.0 | 100 | 95 | 99 | 98 | 86 | 82 |
| 10 mM $Na_3C_5H_6O_7$ - pH 5.0 | 100 | 84 | 86 | 74 | 95 | 41 |
| 10 mM $Na_3C_5H_6O_7$ - pH 6.0 | 100 | 80 | 69 | 51 | 44 | 19 |
| 10 mM $Na_3C_5H_6O_7$ - pH 4.0 with 100 mM $(NH_4)_2SO_4$ | 100 | 95 | 96 | 92 | 82 | 77 |
| 10 mM $Na_3C_5H_6O_7$ - pH 5.0 with 100 mM $(NH_4)_2SO_4$ | 100 | 100 | 101 | 97 | 92 | 89 |
| 10 mM $Na_3C_5H_6O_7$ - pH 6.0 with 100 mM $(NH_4)_2SO_4$ | 100 | 99 | 98 | 95 | 91 | 82 |
| 10 mM $Na_3C_5H_6O_7$ - pH 4.0 with 100 mM NaBr | 100 | 87 | 71 | 46 | 36 | 11 |

These results confirm that the effect of 100 mM $NH_4SO_4$ on the stability of bG-CSF in solution increases as the pH is increased.

The invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and following examples. Such modifications are intended to fall within the scope of the appended claims.

All references cited herein are incorporated by reference in their entireties for all purposes.

What is claimed is:

1. An aqueous composition comprising granulocyte colony stimulating factor and having a pH of from about 5.0 to about 8.0, and a salt comprising sulfate ions, wherein the salt is present at a concentration of from about 0.01M to about 1.0M.

2. The aqueous composition of claim 1, wherein the granulocyte colony stimulating factor is a non-glycosylated granulocyte colony stimulating factor.

3. The aqueous composition of claim 1, wherein the aqueous composition comprises at least about 0.01 mg/ml granulocyte colony stimulating factor.

4. The aqueous composition of claim 1, wherein the aqueous composition comprises at least about 0.1 mg/ml of granulocyte colony stimulating factor.

5. The aqueous composition of claim 1, wherein the aqueous composition comprises at least about 1 mg/ml of granulocyte colony stimulating factor.

6. The aqueous composition of claim 1, further comprising a buffer.

7. The aqueous composition of claim 6, wherein the buffer is a sulfonate buffer.

8. The aqueous composition of claim 7, wherein the sulfonate buffer is selected from the group consisting of HEPES, BES, TAPS, EPPS and mixtures thereof.

9. The aqueous composition of claim 6, wherein the buffer is selected from the group consisting of a phosphate buffer, a citrate buffer, an acetate buffer and mixtures thereof.

10. The aqueous composition of claim 1, wherein the granulocyte colony stimulating factor is selected from the group consisting of bovine granulocyte colony stimulating factor, canine granulocyte colony stimulating factor, feline granulocyte colony stimulating factor, and human granulocyte colony stimulating factor.

11. The aqueous composition of claim 1, wherein the salt is selected from the group consisting of ammonium sulfate, sodium sulfate, magnesium sulfate, and mixtures thereof.

12. The aqueous composition of claim 11, wherein the salt is ammonium sulfate.

13. The aqueous composition of claim 1, wherein the salt comprising sulfate ions is present at a concentration greater than about 0.1M to at least about 1.0M.

14. The aqueous composition of claim 1, wherein the salt comprising sulfate ions is present at a concentration greater than about 0.025M to at least about 0.5M.

15. The aqueous composition of claim 14, wherein the salt comprising sulfate ions is present at a concentration greater than about 0.05M to at least about 0.25M.

16. The aqueous composition of claim 1, wherein the pH is from about 6.0 to about 7.5.

17. The aqueous composition of claim 16, wherein the pH is about 7.0.

18. The aqueous composition of claim 1, wherein the pH is from about 6.0 to about 7.5, the salt comprising sulfate ions is present at a concentration greater than about 0.05M to about 0.25M, and the granulocyte colony stimulating factor concentration is at least about 0.01 mg/mL.

19. The aqueous composition of claim 18, wherein the granulocyte colony stimulating factor is selected from the group consisting of bovine granulocyte colony stimulating factor, canine granulocyte colony stimulating factor, feline granulocyte colony stimulating factor, and human granulocyte colony stimulating factor.

20. A lyophilisate or powder prepared from the aqueous composition of claim 1.

* * * * *